United States Patent
Abe et al.

(10) Patent No.: US 7,763,750 B2
(45) Date of Patent: Jul. 27, 2010

(54) PROCESS FOR PRODUCING 2-HALOGENOBENZAMIDE COMPOUND

(75) Inventors: Noboru Abe, Kawachinagano (JP); Hiroki Kodama, Kawachinagano (JP); Akihiko Yoshiura, Hasaki (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 10/584,221

(22) PCT Filed: Dec. 22, 2004

(86) PCT No.: PCT/JP2004/019234
§ 371 (c)(1), (2), (4) Date: Jun. 20, 2007

(87) PCT Pub. No.: WO2005/063703
PCT Pub. Date: Jul. 14, 2005

(65) Prior Publication Data
US 2007/0293701 A1 Dec. 20, 2007

(30) Foreign Application Priority Data
Dec. 26, 2003 (JP) ............................. 2003-431988

(51) Int. Cl.
- C07C 315/02 (2006.01)
- C07C 315/04 (2006.01)
- C07C 317/28 (2006.01)
- C07B 61/00 (2006.01)

(52) U.S. Cl. ...................... 564/183; 564/161; 564/169; 564/170

(58) Field of Classification Search ...................... None
See application file for complete search history.

(56) References Cited

U.S. PATENT DOCUMENTS 7,057,067 B2 * 6/2006 Kodama et al. ............. 562/493

| 2003/0181759 | A1 | 9/2003 | Kodama et al. |
| 2004/0097595 | A1 | 5/2004 | Nakao et al. |
| 2004/0116299 | A1 * | 6/2004 | Harayama et al. ............ 504/335 |

FOREIGN PATENT DOCUMENTS

| EP | 1277726 A1 | 1/2003 |
| EP | 1389613 A1 | 2/2004 |
| JP | 2002-338516 | 11/2002 |
| JP | 2003-12638 A | 1/2003 |
| WO | WO 02/088075 A1 | 11/2002 |

* cited by examiner

Primary Examiner—Daniel M Sullivan
Assistant Examiner—Yevegeny Valenrod
(74) Attorney, Agent, or Firm—Paul E. White, Jr.; Manelli Dennison & Selter PLLC

(57) ABSTRACT

A novel process for producing a 2-halogenobenzamide compound useful as a raw material or active ingredient for medicines and agricultural chemicals. The process, which is for producing a 2-halogenobenzamide compound represented by the general formula (I):

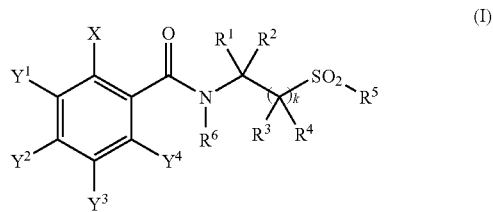

(wherein $R^1$, $R^2$, $R^3$, $R^4$, and $R^6$ may be the same or different and each represents hydrogen or $C_{1-6}$ alkyl; $R^5$ represents $C_{1-6}$ alkyl; k is 1 or 2; $Y^1$, $Y^2$, $Y^3$, and $Y^4$ may be the same or different and each represents hydrogen, halogeno, etc.; and X represents chlorine, bromine, or iodine), is characterized by reacting an benzamide compound with a halogenating agent in the presence of a palladium catalyst to obtain a substituted benzamide compound and then reacting the resultant substituted benzamide compound with an oxidizing agent after or without isolating the substituted benzamide compound.

4 Claims, No Drawings

PROCESS FOR PRODUCING 2-HALOGENOBENZAMIDE COMPOUND

This application is the national phase of international application PCT/JP2004/019234 filed 22 Dec. 2004 which designated the U.S.

TECHNICAL FIELD

The present invention relates to a novel process for producing a 2-halogenobenzamide compound useful as a starting material or active ingredient for medicines and agrochemicals.

BACKGROUND ART

The 2-halogenobenzamide compound according to the present invention is known to be producible by allowing a corresponding benzoic acid derivative or the like as a starting material to react with a suitable amine or aniline derivative in succession (see, for example, patent document 1, patent document 2, patent document 3, patent document 4 and patent document 5). These references, however, do not disclose the production process of the present invention. In addition, although processes for producing the corresponding starting material or intermediate are known (see, for example, patent document 6 and patent document 7), these references neither describe nor suggest the usefulness of the production process of the present invention.

Patent document 1: JP-A-11-240857 ("Phthalic Acid Diamide Derivatives, Agricultural and Horticultural Insecticides and Method of Using the Same").

Patent document 2: JP-A-2001-131141 ("Phthalamide Derivatives or Salts Thereof, Agricultural and Horticultural Insecticides and Method of Using the Same").

Patent document 3: JP-A-2001-335563 ("Phthalamide Derivatives, Intermediates Thereof, Agricultural and Horticultural Insecticides and Method of Using the Same").

Patent document 4: JP-A-2003-034673 ("Substituted Aromatic Amide Derivatives, Intermediates Thereof, Agricultural and Horticultural Insecticides and Method of Using the Same").

Patent document 5: JP-A-2003-12638 ("Phthalamide Derivatives, Agricultural and Horticultural Insecticides and Method of Using the Same").

Patent document 6: JP-A-2002-338516 ("Process for Producing 2-Halogenobenzoic Acid Compound").

Patent document 7: JP-A-2002-326989 ("Process for Producing Phthalisoimide Derivative").

DISCLOSURE OF THE INVENTION

Problem to be Solved by the Invention

When the 2-halogenobenzamide compound according to the present invention is produced by a well-known process, regioisomers having a substituent at an undesirable position are always produced in addition to the desired 2-halogenobenzamide compound. As a result, the purity of the desired compound is often decreased. Moreover, in some cases, some treatment for removing or reducing the regioisomers causes a remarkable yield decrease and hence a decrease of economical benefit.

The present invention is intended to provide a novel and very economical process for producing a 2-halogenobenzamide compound having a sulfonyl group in its amide side chain.

Means for Solving the Problem

The present inventors earnestly investigated in order to solve the above problems, and consequently found a production process comprising a series of steps which is characterized in that in the production of a substituted benzamide compound represented by general formula (I), a benzamide compound represented by general formula (II) is allowed to react with a halogenating agent in the presence of a catalytic amount of a palladium catalyst to obtain a halogeno-benzamide derivative represented by general formula (III) by regioselective halogenation, followed by oxidizing the halogenobenzamide derivative represented by general formula (III), whereby the present invention has been accomplished.

That is, the present invention relates to a process for producing a 2-halogenobenzamide compound represented by general formula (I):

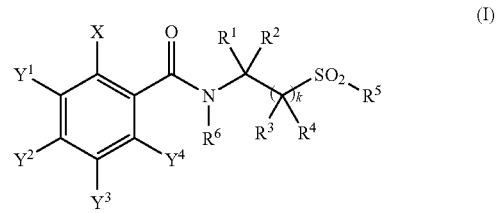

(wherein X, $R^1$, $R^2$, $R^3$, $R^4$, $R^5$, $R^6$, $Y^1$, $Y^2$, $Y^3$, $Y^4$ and k are as defined below), characterized by allowing a halogenating agent to react with a benzamide compound represented by the following general formula (II):

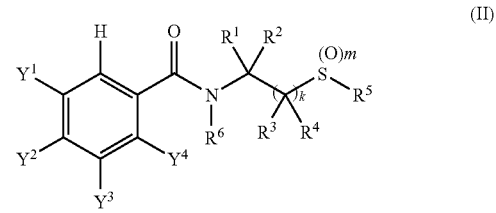

(wherein each of $R^1$, $R^2$, $R^3$, $R^4$ and $R^6$, which may be the same or different, is a hydrogen atom or a ($C_1$-$C_6$)alkyl group, $R^5$ is a ($C_1$-$C_6$)alkyl group, k is 1 or 2, m is 0 or 1, and each of $Y^1$, $Y^2$, $Y^3$ and $Y^4$, which may be the same or different, is a hydrogen atom; a halogen atom; a cyano group; a nitro group; a ($C_1$-$C_6$)alkyl group; a ($C_1$-$C_6$)alkylcarbonyl group; a carboxyl group; a ($C_1$-$C_{12}$)alkoxycarbonyl group; a phenylcarbonyl group; a substituted phenylcarbonyl group having one or more substituents which may be the same or different and are selected from halogen atoms, cyano group, nitro group, ($C_1$-$C_6$)alkyl groups, ($C_1$-$C_6$)alkoxy groups, halo($C_1$-$C_6$)alkyl groups and halo($C_1$-$C_6$)alkoxy groups; a benzylcarbonyl group; a substituted benzylcarbonyl group having on the ring one or more substituents which may be the same or different and are selected from halogen atoms, cyano group, nitro group, ($C_1$-$C_6$)alkyl groups, ($C_1$-$C_6$)alkoxy groups, halo($C_1$-$C_6$)alkyl groups and halo($C_1$-$C_6$)alkoxy groups;

—CON($R^7$)$R^8$ (wherein each of $R^7$ and $R^8$, which may be the same or different, is a hydrogen atom; a ($C_1$-$C_6$)alkyl group; a phenyl group; a substituted phenyl group having one or more substituents which may be the same or different and are selected from halogen atoms, cyano group, nitro group, ($C_1$-$C_6$)alkyl groups, ($C_1$-$C_6$)alkoxy groups, halo($C_1$-$C_6$)alkyl groups and halo($C_1$-$C_6$)alkoxy groups; a pyridyl group; a substituted pyridyl group having one or more substituents which may be the same or different and are selected from hydrogen atom, halogen atoms, cyano group, nitro group, ($C_1$-$C_6$)alkyl groups, ($C_1$-$C_6$)alkoxy groups, halo($C_1$-$C_6$)alkyl groups and halo($C_1$-$C_6$)alkoxy groups; a benzyl group; or a substituted benzyl group having on the ring one or more substituents which may be the same or different and are selected from halogen atoms, cyano group, nitro group, ($C_1$-$C_6$)alkyl groups, ($C_1$-$C_6$)alkoxy groups, halo($C_1$-$C_6$)alkyl groups and halo($C_1$-$C_6$)alkoxy groups); —N($R^7$)—$COR^8$ (wherein $R^7$ and $R^8$ are as defined above); a phenyl group; a substituted phenyl group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$)alkoxy groups and halo($C_1$-$C_6$)alkoxy groups;

a phenoxy group; a substituted phenoxy group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$) alkoxy groups and halo($C_1$-$C_6$)alkoxy groups; a heteroaryloxy group; or a substituted heteroaryloxy group having one or more substituents which may be the same or different and are selected from halogen atoms, cyano group, nitro group, ($C_1$-$C_6$)alkyl groups, halo($C_1$-$C_6$)alkyl groups, ($C_1$-$C_6$) alkoxy groups and halo($C_1$-$C_6$)alkoxy groups, any adjacent two members of a group consisting of $Y^1$, $Y^2$, $Y^3$ and $Y^4$ being able to bind to each other to form a fused ring comprising a ($C_3$-$C_4$)alkylene group or a ($C_3$-$C_4$)alkenylene group, which may have on the ring one or more substituents which may be the same or different and are selected from halogen atoms; cyano group; nitro group; ($C_1$-$C_6$)alkyl groups; ($C_1$-$C_6$)alkylcarbonyl groups; carboxyl group; ($C_1$-$C_{12}$)alkoxycarbonyl groups; phenyl group; substituted phenyl groups having one or more substituents which may be the same or different and are selected from halogen atoms, cyano group, nitro group, ($C_1$-$C_6$)alkyl groups, ($C_1$-$C_6$)alkoxy groups, halo($C_1$-$C_6$) alkyl groups and halo($C_1$-$C_6$)alkoxy groups; benzyl group; and substituted benzyl groups having on the ring one or more substituents which may be the same or different and are selected from halogen atoms, cyano group, nitro group, ($C_1$-$C_6$)alkyl groups, ($C_1$-$C_6$)alkoxy groups, halo($C_1$-$C_6$)alkyl groups and halo($C_1$-$C_6$)alkoxy groups) in the presence of a palladium catalyst to obtain a substituted benzamide compound represented by general formula (III):

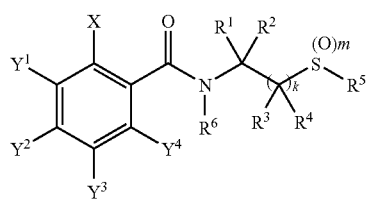

(III)

(wherein X is a chlorine atom, a bromine atom or an iodine atom, and $R^1$, $R^2$, $R^3$, $R^4$, $R^5$, $R^6$, $Y^1$, $Y^2$, $Y^3$, $Y^4$, k and m are as defined above), and then allowing the substituted benzamide compound of general formula (III) obtained, to react with an oxidizing agent after or without isolating the compound.

Advantages of the Invention

According to the present invention, a substituted benzamide compound having a halogen atom as the substituent at a desired position with high selectivity can be produced and provided easily at low cost.

BEST MODE FOR CARRYING OUT THE INVENTION

The present invention is explained below in detail.

In the definition of the 2-halogenobenzamide compound of general formula (I) according to the present invention, the term "halogen atom" means a chlorine atom, a bromine atom, an iodine atom or a fluorine atom. The term "($C_1$-$C_6$)alkyl" means a linear or branched alkyl group of 1 to 6 carbon atoms, such as methyl, ethyl, n-propyl, i-propyl, n-butyl, i-butyl, s-butyl, t-butyl, n-pentyl, n-hexyl or the like. The term "halo($C_1$-$C_6$)alkyl" means a substituted linear or branched alkyl group of 1 to 6 carbon atoms having as the substituent(s) one or more halogen atoms which may be the same or different. The term "($C_3$-$C_4$)alkylene" means a linear or branched alkylene group of 3 to 4 carbon atoms, such as propylene, trimethylene, methylpropylene, tetramethylene or the like. The term "($C_3$-$C_4$)alkenylene" means a linear or branched alkenylene group of 3 to 4 carbon atoms having a double bond in the molecule.

The term "heteroaryloxy group" means a 6-membered heterocyclyloxy group having 1 to 3 nitrogen atoms on the ring. The heteroaryloxy group includes, for example, 2-pyridyloxy group, 3-pyridyloxy group, 4-pyridyloxy group, 3-pyridazinyloxy group, 4-pyridazinyloxy group, 2-pyrimidinyloxy group, 4-pyrimidinyloxy group, 5-pyrimidinyloxy group, 2-pyrazinyloxy group and 2-triazinyloxy group.

The process for producing a 2-halogenobenzamide compound of the present invention is schematically shown below.

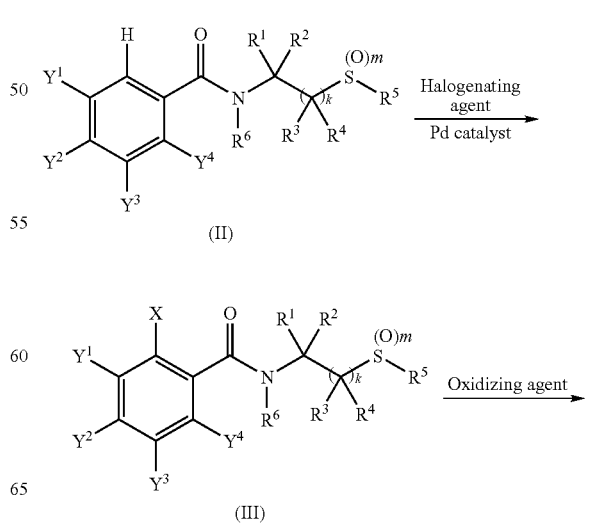

-continued

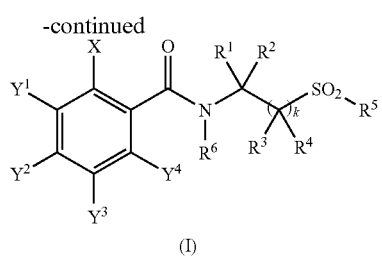

(I)

wherein X, $R^1$, $R^2$, $R^3$, $R^4$, $R^5$, $R^6$, $Y^1$, $Y^2$, $Y^3$, $Y^4$, k and m are as defined above.

That is, a benzamide compound represented by general formula (II) is allowed to react with a halogenating agent in the presence of a palladium catalyst and in the presence or absence of a suitable inert solvent to obtain a substituted benzamide compound represented by general formula (III), and this substituted benzamide derivative (III) is allowed to react with an oxidizing agent in the presence or absence of a suitable inert solvent and in the presence or absence of a catalyst after or without isolation of the derivative, whereby a substituted benzamide compound represented by general formula (I) can be produced. The present invention is characterized by using a benzamide compound having a sulfide or a sulfoxide in its amide side chain, as a starting material, halogenating its benzene ring, and then oxidizing the sulfide or sulfoxide. Particularly in the halogenation step, a high regioselectivity, a high catalyst turnover and a high yield can be attained.

General Formula (II)→General Formula (III)

As the palladium catalyst usable in this reaction, there can be used divalent palladiums such as palladium acetate, palladium chloride, palladium iodide, palladium nitrate, palladium acetylacetonate, etc.; and palladium complexes obtained by coordination of any of these divalent palladiums with a ligand such as acetonitrile, triphenylphosphine, benzonitrile or the like. These palladium catalysts may be used singly or as a mixture of two or more thereof. The amount of the palladium catalyst used may be a catalytic amount with respect to the benzamide compound of general formula (II) and is usually about 1/100000 equivalent to about 1/2 equivalent, preferably about 1/100000 equivalent to about 1/10 equivalent, more preferably about 1/10000 equivalent to about 1/100 equivalent, per equivalent of the benzamide compound of general formula (II).

As the halogenating agent usable in the reaction, there can be used molecular halogens such as $I_2$, $Cl_2$, $Br_2$, ICl, etc.; and compounds having a halogen atom bonded to an element in group 15 of the periodic table, such as N-chlorosuccinimide, N-iodosuccinimide, 1,3-diiodohydantoin, 1,3-dichloro-5,5-dimethylhydantoin, 1,3-dibromo-5,5-dimethylhydantoin, 1,3-diiodo-5,5-dimethylhydantoin, etc. As to the amount of the halogenating agent used, the halogenating agent may be used in an amount of 1/2 equivalent to excess equivalents per equivalent of the benzamide compound of general formula (II). The amount is preferably about 1 equivalent to about 3 equivalents, more preferably about 1 equivalent to about 1.5 equivalents, per equivalent of the benzamide compound of general formula (II).

The inert solvent usable in the reaction is not particularly limited and may be any inert solvent so long as it does not markedly inhibit the progress of the reaction. As the inert solvent, there can be used, for example, organic acid solvents such as acetic acid, etc.; ether solvents such as dioxane, tetrahydrofuran, diethyl ether, etc.; nitrile solvents such as acetonitrile, propionitrile, etc.; amide solvents such as N,N-dimethylformamide, N,N-dimethylacetamide, N-methylpyrrolidone, etc.; aromatic solvents such as toluene, etc.; ester solvents such as ethyl acetate, etc.; ketone solvents such as methyl ethyl ketone, etc.; halogenated hydrocarbon solvents such as chloroform, dichloromethane, etc.; and water. These solvents may be used singly or as a mixture of two or more thereof.

As to the reaction temperature for the above reaction, the reaction can be carried out in the range of room temperature to the boiling point of the solvent. The reaction temperature is preferably in the range of about 40° C. to about 200° C., more preferably about 50° C. to about 120° C. If necessary, additives such as a solubilizing agent, auxiliary catalyst, oxidizing agent, coordination compound, metal salt and the like may be used in the reaction. The additives include, for example, sodium acetate, copper acetate, benzonitrile, triphenylphosphine, periodic acid, hydrogen peroxide and water.

After completion of the reaction, the desired compound is isolated from the reaction system containing the desired compound by a conventional method, and if necessary, purified by recrystallization, column chromatography, etc., whereby the desired compound can be produced. Alternatively, the desired compound can be subjected to the subsequent step without isolation by purifying the desired compound by concentration, extraction, washing and/or separation, etc. if necessary.

General Formula (III)→General Formula (I)

The oxidizing agent usable in this reaction includes, for example, peracids (e.g. m-chloroperbenzoic acid, peracetic acid and performic acid), potassium metaperiodate, sodium hypochlorite, potassium hydrogenpersulfate (Oxon, a trade name), sodium persulfate, potassium persulfate, ammonium persulfate, hydrogen peroxide, sodium perborate, N-chlorosuccinimide and N-bromosuccinimide. The amount of the oxidizing agent used is varied depending on the compound chosen as a substrate between the sulfide compound and the sulfoxide compound. When the compound as substrate is the sulfide compound, the oxidizing agent may be used in an amount properly chosen in the range of 2 to 5 equivalents per equivalent of the substituted benzamide derivative of general formula (III). When the compound as substrate is the sulfoxide compound, the oxidizing agent may be used in an amount properly chosen in the range of 1 to 2 equivalents per equivalent of the substituted benzamide derivative of general formula (III).

As the inert solvent usable in the reaction, any inert solvent may be used so long as it does not markedly inhibit the progress of the reaction. There can be used, for example, halogenated hydrocarbon solvents such as methylene chloride, chloroform, dichloroethane, chlorobenzene, etc.; nitrites such as acetonitrile, propionitrile, etc.; aliphatic hydrocarbon solvents such as hexane, heptane, etc.; aromatic hydrocarbon solvents such as toluene, xylene, etc.; organic acid solvents such as acetic acid, etc.; alcohol solvents such as methanol, ethanol, butanol, etc.; ester solvents such as ethyl acetate, butyl acetate, etc.; amide solvents such as N,N-dimethylformamide, N,N-dimethylacetamide, N-methylpyrrolidone, etc.; and water. These solvents may be used singly or as a mixture of two or more thereof.

As the catalyst usable in the reaction, there can be used tungstic acid, molybdic acid, vanadic acid, their salts, organic acids and inorganic acids. The organic acids include, for example, carboxylic acids such as formic acid, acetic acid, propionic acid, butyric acid, oxalic acid, adipic acid, dodecanedicarboxylic acid, lauric acid, stearic acid, trifluoroacetic acid, fumaric acid, maleic acid, benzoic acid, phthalic acid, etc.; and sulfonic acids such as methanesulfonic acid, 1,3-propanedisulfonic acid, p-toluenesulfonic acid, dodecylbenzenesulfonic acid, etc. The inorganic acids include sulfuric acid, boric acid and the like. The amount of the catalyst used is usually about 1/10000 equivalent to about 3 equivalents, preferably about 1/1000 equivalent to about 1 equivalent, per equivalent of the benzamide compound of general formula (III). The above-exemplified catalysts may be used singly or as a mixture of two or more thereof. It is also possible to carry out the reaction without using any catalyst.

As to the reaction temperature, the reaction may be carried out in the range of −50° C. to the boiling point of the solvent used. Although the reaction time is varied depending on the scale of reaction, the reaction temperature and the like, it ranges from several minutes to 48 hours. After completion of the reaction, to isolate the compound of general formula (I), i.e., the desired compound, it is sufficient that the compound in the reaction mixture is crystallized, followed by filtration and/or water-washing. Thus, the compound of general formula (I), the desired compound can be obtained. Although the compound obtained has a satisfactory quality as it is in some cases, it can, if necessary, be purified by a means such as washing or recrystallization by the use of the above-exemplified solvent for reaction.

The compound of the above general formula (II) as intermediate can be produced according to a well-known process. As this compound, a compound of general formula (II-1) or (II-1') in which $Y^4$ is —CON($R^7$)$R^8$ can be produced according to the process disclosed in any of the above-mentioned patent documents 1 to 7 or the like, for example, either of the following production processes 1 and 2.

Production Process 1:

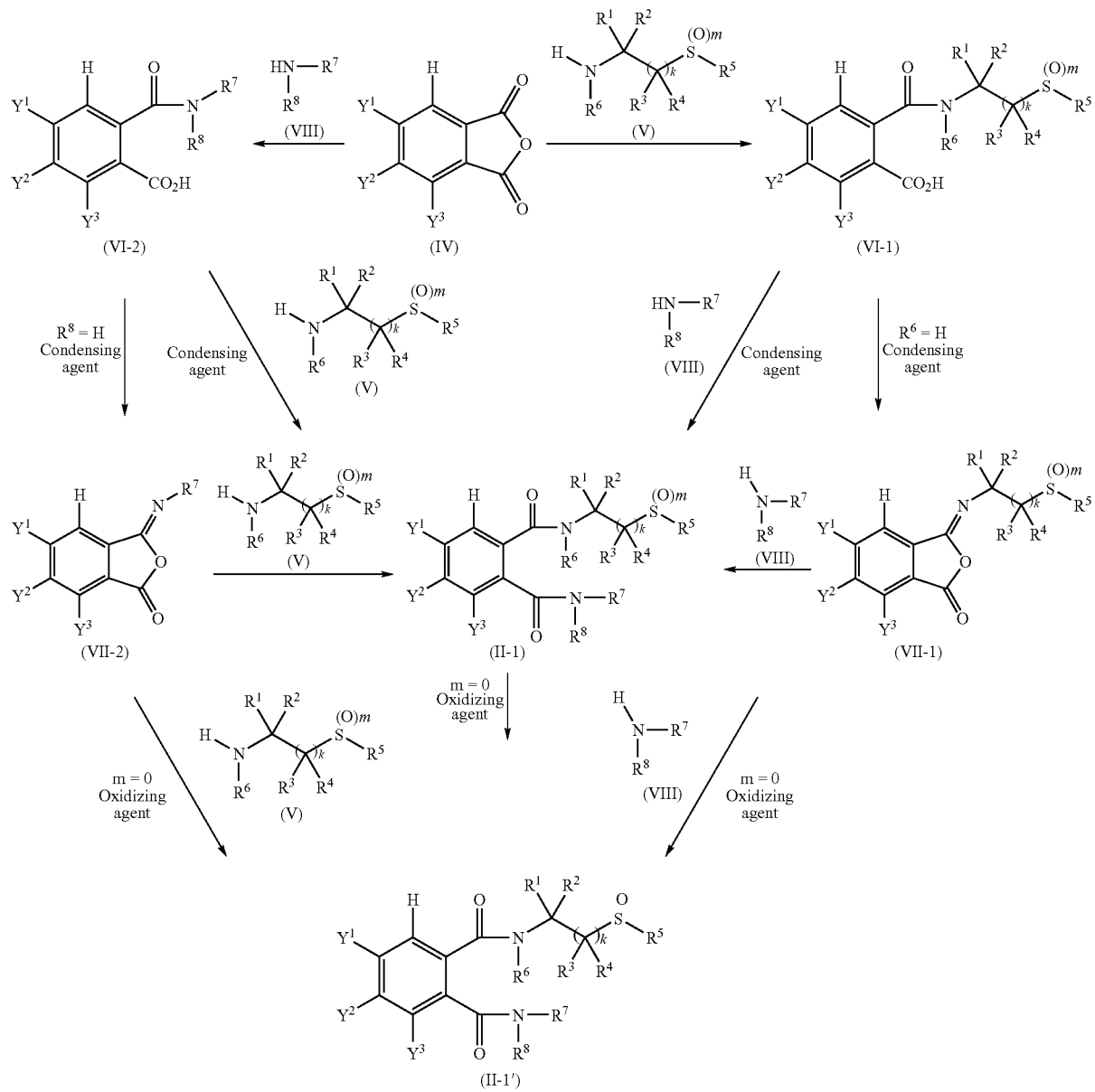

wherein $R^1, R^2, R^3, R^4, R^5 R^6, R^7, R^8, Y^1, Y^2, Y^3, Y^4$, k and m are as defined above.

A phthalic anhydride derivative of general formula (IV) is allowed to react with an amine of general formula (V) in the presence or absence of an inert solvent and a base to obtain a compound of general formula (VI-1). In the case of a compound (VI-1) in which $R^6$ is a hydrogen atom, this compound (VI-1) is condensed in the presence of a condensing agent in an inert solvent in the presence or absence of a base after or without isolation of the compound to obtain a compound of general formula (VII-1). The compound (VII-1) is allowed to react with an amine derivative of general formula (VIII) in the presence of an inert solvent and in the presence or absence of a catalyst after or without isolation of the compound (VII-1), whereby a benzamide compound of general formula (II-1) can be produced. In the case of a compound (VI-1) in which $R^6$ is a substituent other than a hydrogen atom, this compound (VI-1) is condensed with an amine of general formula (VIII) in the presence of a condensing agent in an inert solvent in the presence or absence of a base after or without isolation of the compound (VI-1), whereby a benzamide compound of general formula (II-1) can be produced.

In addition, a phthalic anhydride derivative of general formula (IV) is allowed to react with an amine of general formula (VIII) in the presence or absence of an inert solvent and a base to obtain a compound of general formula (VI-2). In the case of a compound (VI-2) in which $R^8$ is a hydrogen atom, this compound (VI-2) is condensed in the presence of a condensing agent in an inert solvent in the presence or absence of a base after or without isolation of the compound to obtain a compound of general formula (VII-2). The compound (VII-2) is allowed to react with an amine derivative of general formula (V) in the presence of an inert solvent and in the presence or absence of a catalyst after or without isolation of the compound (VII-2), whereby a benzamide compound of general formula (II-1) can be produced. In the case of a compound (VI-2) in which $R^8$ is a substituent other than a hydrogen atom, this compound (VI-2) is condensed with an amine of general formula (V) in the presence of a condensing agent in an inert solvent in the presence or absence of a base after or without isolation of the compound (VI-2), whereby a benzamide compound of general formula (II-1) can be produced.

Furthermore, a compound represented by general formula (II-1') corresponding to general formula (II-1) in which m is defined as 1 can be produced by oxidizing a compound of general formula (II-1) in which m is 0 with an oxidizing agent in an inert solvent in the presence or absence of a catalyst after or without isolation of the compound. The compound of general formula (II-1') can be produced also by allowing an amine of general formula (VIII) and an oxidizing agent to react at the same time or alternately with a compound of general formula (VII-1) in which m is defined as 0, in an inert solvent in the presence or absence of a catalyst after or without isolation of the compound of general formula (VII-1). In addition, the compound of general formula (II-1') can be produced also by allowing an amine of general formula (V) in which m is defined as 0 and an oxidizing agent to react at the same time or alternately with the compound of general formula (VII-2) in an inert solvent in the presence or absence of a catalyst after or without isolation of the compound of general formula (VII-2).

1-1. General Formula (IV)→General Formula (VI-1) or General Formula (VI-2)

The inert solvent usable in this reaction is not particularly limited so long as it does not directly participate in the reaction. The inert solvent includes, for example, aromatic hydrocarbon solvents such as benzene, toluene, xylene, etc.; ketone solvents such as acetone, methyl ethyl ketone, methyl isobutyl ketone, etc.; halogenated hydrocarbon solvents such as chloroform, dichloromethane, 1,2-dichloroethane, chlorobenzene, etc.; ester solvents such as methyl acetate, ethyl acetate, etc.; ether solvents such as diethyl ether, tetrahydrofuran, dioxane, etc.; nitrile solvents such as acetonitrile, etc.; amide solvents such as N,N-dimethylformamide, N,N-dimethylacetamide, N-methylpyrrolidone, etc.; and polar solvents such as dimethyl sulfoxide, water, pyridine, etc. These inert solvents may be used singly or as a mixture of two or more thereof.

The base usable in the reaction includes, for example, hydrides of alkali metals, such as sodium hydride, etc.; hydroxides of alkali metals, such as sodium hydroxide, potassium hydroxide, etc.; carbonates of alkali metals, such as sodium carbonate, potassium carbonate, etc.; and organic bases such as pyridine, DBU (1,8-diazabicyclo[5.4.0]-7-undecene), triethylamine, etc. As to the amount of the base used, the reaction may be carried out by choosing the amount generally in the range of a catalytic amount to excess moles per mole of the phthalic anhydride of formula (IV).

As to the reaction temperature, the reaction may be properly carried out in the range of −50° C. to the boiling point of the inert solvent used. The reaction temperature is preferably in the range of 0° C. to 60° C. Although the reaction time is varied depending on the scale of reaction and the reaction temperature, it ranges from several minutes to 48 hours.

Since the reaction is an equimolar reaction, it is sufficient that the acid anhydride of general formula (IV) and the amine of general formula (V) or general formula (VIII) are used in equimolar amounts, though either of the reactants may be used in excess. It is preferable to use the amine (V) or (VIII) in a slight excess.

After the reaction, the reaction solution can be subjected as it is to reaction in the subsequent step without isolating the compound of general formula (VI-1) or (VI-2). When the isolation and/or purification of this desired compound are necessary, the desired compound is isolated from the reaction system containing the desired compound by a conventional method after completion of the reaction, and if necessary, purified by recrystallization, column chromatography, etc., whereby the compound of general formula (VI-1) or (VI-2) can be produced.

The compound (V) as intermediate can be synthesized according to the process disclosed in JP-A-2001-163854 or JP-A-2002-105046.

1-2. General Formula (VI-1) or General Formula (VI-2)→General Formula (II-1)

The inert solvent usable in this reaction is not particularly limited so long as it does not directly participate in the reaction. The inert solvent includes, for example, aromatic hydrocarbon solvents such as benzene, toluene, xylene, etc.; ketone solvents such as acetone, methyl ethyl ketone, methyl isobutyl ketone, etc.; halogenated hydrocarbon solvents such as chloroform, dichloromethane, 1,2-dichloroethane, chlorobenzene, etc.; ester solvents such as methyl acetate, ethyl acetate, etc.; ether solvents such as diethyl ether, tetrahydrofuran, dioxane, etc.; nitrile solvents such as acetonitrile, etc.; amide solvents such as N,N-dimethylformamide, N,N-dimethylacetamide, N-methylpyrrolidone, etc.; and polar solvents such as dimethyl sulfoxide, pyridine, etc. These inert solvents may be used singly or as a mixture of two or more thereof.

As the condensing agent used in the reaction, any condensing agent may be used so long as it is used in conventional amide production. The condensing agent includes, for example, Mukaiyama reagent (2-chloro-N-methylpyridinium iodide), DCC (1,3-dicyclohexylcarbodiimide), CDI (carbonyl diimidazole) and DEPC (diethyl cyanophosphate). As to the amount of the condensing agent used, the condensing agent may be used in an amount properly chosen in the range of 1 mole to excess moles per mole of the phthalamide compound of general formula (VI-1) or (VI-2). The base usable in the reaction includes, for example, hydroxides of alkali metals, such as sodium hydroxide, potassium hydroxide, etc.; carbonates of alkali metals, such as sodium carbonate, potassium carbonate, etc.; and organic bases such as pyridine, DBU (1,8-diazabicyclo[5.4.0]-7-undecene), triethylamine, etc. As to the amount of the base used, the reaction may be carried out by choosing the amount generally in the range of 1 mole to excess moles per mole of the phthalamide compound of general formula (VI-1) or (VI-2).

As to the reaction temperature, the reaction may be properly carried out in the range of −50° C. to the boiling point of the inert solvent used. The reaction temperature is preferably in the range of 0° C. to 60° C. Although the reaction time is varied depending on the scale of reaction and the reaction temperature, it ranges from several minutes to 48 hours.

Since the reaction is an equimolar reaction, it is sufficient that the phthalamide compound of general formula (VI-1) or general formula (VI-2) and the amine of general formula (V) or general formula (VIII) are used in equimolar amounts, though either of the reactants may be used in excess.

After the reaction, the reaction solution can be subjected as it is to reaction in the subsequent step without isolating the compound of general formula (II-1). When the isolation and/or purification of this desired compound are necessary, the desired compound is isolated from the reaction system containing the desired compound by a conventional method after completion of the reaction, and if necessary, purified by recrystallization, column chromatography, etc., whereby the compound of general formula (II-1) can be produced.

1-3. General Formula (VI-1)→General Formula (VII-1), or General Formula (VI-2)→General Formula (VII-2)

In the Case of this reaction, the desired compound can be produced according to, for example, the process described in J. Med. Chem., 10, 982 (1967). As the dehydrating-condensation agent usable in the reaction, there can be used, for example, acid anhydrides such as acetic anhydride, trifluoroacetic anhydride, etc.; and chloroformic acid esters such as methyl chloroformate, ethyl chloroformate, etc. As to the amount of the dehydrating-condensation agent used, the reaction may be carried out by properly choosing the amount in the range of 1 mole to excess moles per mole of the compound of general formula (VI-1) or (VI-2).

The base usable in the reaction includes, for example, hydroxides of alkali metals, such as sodium hydroxide, potassium hydroxide, etc.; carbonates of alkali metals, such as sodium carbonate, potassium carbonate, etc.; and organic bases such as pyridine, DBU (1,8-diazabicyclo[5.4.0]-7-undecene), triethylamine, etc. As to the amount of the base used, the reaction may be carried out by choosing the amount in the range of 1 mole to excess moles per mole of the compound of general formula (VI-1) or (VI-2).

The inert solvent usable in the reaction is not particularly limited so long as it does not directly participate in the reaction. The inert solvent includes, for example, aromatic hydrocarbon solvents such as benzene, toluene, xylene, etc.; ketone solvents such as acetone, methyl ethyl ketone, methyl isobutyl ketone, etc.; halogenated hydrocarbon solvents such as chloroform, dichloromethane, 1,2-dichloroethane, chlorobenzene, etc.; ester solvents such as methyl acetate, ethyl acetate, etc.; ether solvents such as diethyl ether, methyl t-butyl ether, tetrahydrofuran, dioxane, etc.; nitrile solvents such as acetonitrile, etc.; amide solvents such as N,N-dimethylformamide, N,N-dimethylacetamide, N-methylpyrrolidone, etc.; and polar solvents such as dimethyl sulfoxide, water, pyridine, etc. These inert solvents may be used singly or as a mixture of two or more thereof.

As to the reaction temperature, the reaction may be carried out in the range of −50° C. to the boiling point of the inert solvent used. The reaction temperature is preferably in the range of 0° C. to 60° C. Although the reaction time is varied depending on the scale of reaction and the reaction temperature, it ranges from several minutes to 48 hours.

After completion of the reaction, the reaction solution can be subjected as it is to reaction in the subsequent step without isolating the compound of general formula (VII-1) or (VII-2). When the isolation and/or purification of this desired compound are necessary, the desired compound is isolated from the reaction system containing the desired compound by a conventional method after completion of the reaction, and if necessary, purified by recrystallization, column chromatography, etc., whereby the compound of general formula (VII-1) or (VII-2) can be produced.

1-4. General Formula (VII-1) or General Formula (VII-2)→General Formula (II-1)

The inert solvent usable in this reaction is not particularly limited so long as it does not directly participate in the reaction. The inert solvent includes, for example, aromatic hydrocarbon solvents such as benzene, toluene, xylene, etc.; ketone solvents such as acetone, methyl ethyl ketone, methyl isobutyl ketone, etc.; halogenated hydrocarbon solvents such as chloroform, dichloromethane, 1,2-dichloroethane, chlorobenzene, etc.; ester solvents such as methyl acetate, ethyl acetate, etc.; ether solvents such as diethyl ether, methyl t-butyl ether, tetrahydrofuran, dioxane, etc.; nitrile solvents such as acetonitrile, etc.; amide solvents such as N,N-dimethylformamide, N,N-dimethylacetamide, N-methylpyrrolidone, etc.; and polar solvents such as dimethyl sulfoxide, water, pyridine, etc. These inert solvents may be used singly or as a mixture of two or more thereof.

As the catalyst usable in the reaction, organic acids and inorganic acids can be used. The organic acids include, for example, carboxylic acids such as acetic acid, propionic acid, butyric acid, oxalic acid, adipic acid, dodecanedicarboxylic acid, lauric acid, stearic acid, trifluoroacetic acid, fumaric acid, maleic acid, benzoic acid, phthalic acid, etc.; and sulfonic acids such as methanesulfonic acid, 1,3-propanedisulfonic acid, p-toluenesulfonic acid, dodecylbenzenesulfonic acid, etc. The inorganic acids include hydrochloric acid, sulfuric acid, nitric acid, carbonic acid and the like. As to the amount of the catalyst used, the reaction may be carried out by properly choosing the amount generally in the range of a catalytic amount to excess moles per mole of the compound of formula (VII-1) or formula (VII-2).

As to the reaction temperature, the reaction may be properly carried out in the range of −50° C. to the boiling point of the inert solvent used. The reaction temperature is preferably in the range of 0° C. to 60° C. Although the reaction time is varied depending on the scale of reaction and the reaction temperature, it ranges from several minutes to 48 hours.

Since the reaction is an equimolar reaction, it is sufficient that the compound of general formula (VII-1) or general formula (VII-2) and the amine of general formula (V) or general formula (VIII) are used in equimolar amounts, though either of the reactants may be used in excess.

After completion of the reaction, the reaction solution can be subjected as it is to reaction in the subsequent step without isolating the compound of general formula (II-1), i.e., the desired compound. When the isolation and/or purification of the desired compound are necessary, the desired compound in the reaction mixture is crystallized, followed by filtration and/or water-washing. Thus, the compound of general formula (II-1), the desired compound can be obtained. Although the compound obtained has a satisfactory quality as it is in some cases, it can, if necessary, be purified by a means such as washing or recrystallization by the use of the above-exemplified solvent for reaction.

1-5. General Formula (II-1)→General Formula (II-1')

As the inert solvent usable in this reaction, any inert solvent may be used so long as it does not markedly inhibit the progress of the reaction. There can be used, for example, halogenated hydrocarbon solvents such as methylene chloride, chloroform, dichloroethane, chlorobenzene, etc.; nitrile solvents such as acetonitrile, propionitrile, etc.; aliphatic hydrocarbon solvents such as hexane, heptane, etc.; aromatic hydrocarbon solvents such as toluene, xylene, etc.; organic acid solvents such as acetic acid, etc.; alcohol solvents such as methanol, ethanol, butanol, etc.; ester solvents such as ethyl acetate, butyl acetate, etc.; amide solvents such as N,N-dimethylformamide, N,N-dimethylacetamide, N-methylpyrrolidone, etc.; and water. These solvents may be used singly or as a mixture of two or more thereof.

The oxidizing agent includes, for example, peracids (e.g. m-chloroperbenzoic acid, peracetic acid and performic acid), potassium metaperiodate, sodium hypochlorite, potassium hydrogenpersulfate (Oxon), sodium persulfate, potassium persulfate, ammonium persulfate, hydrogen peroxide, sodium perborate, N-chlorosuccinimide and N-bromosuccinimide. As to the amount of the oxidizing agent used, the oxidizing agent may be used in an amount properly chosen in the range of 1 to 2 equivalents per equivalent of the compound of general formula (II-1) in which m is defined as 0.

As the catalyst, there can be used tungstic acid, molybdic acid, vanadic acid, their salts, organic acids and inorganic acids. The organic acids include, for example, carboxylic acids such as formic acid, acetic acid, propionic acid, butyric acid, oxalic acid, adipic acid, dodecanedicarboxylic acid, lauric acid, stearic acid, trifluoroacetic acid, fumaric acid, maleic acid, benzoic acid, phthalic acid, etc.; and sulfonic acids such as methanesulfonic acid, 1,3-propanedisulfonic acid, p-toluenesulfonic acid, dodecylbenzenesulfonic acid, etc. The inorganic acids include sulfuric acid, boric acid and the like. The amount of the catalyst used is usually about 1/10000 equivalent to about 3 equivalents, preferably about 1/1000 equivalent to about 1 equivalent, per equivalent of the compound of general formula (II-1). The above-exemplified catalysts may be used singly or as a mixture of two or more thereof.

As to the reaction temperature, the reaction may be carried out in the range of −50° C. to the boiling point of the solvent used. Although the reaction time is varied depending on the scale of reaction, the reaction temperature and the like, it ranges from several minutes to 48 hours.

After completion of the reaction, the reaction solution can be subjected as it is to reaction in the subsequent step without isolating the compound of general formula (II-1'), i.e., the desired compound. When the isolation and/or purification of the desired compound are necessary, the desired compound in the reaction mixture is crystallized, followed by filtration and/or water-washing. Thus, the compound of general formula (II-1'), the desired compound can be obtained. Although the compound obtained has a satisfactory quality as it is in some cases, it can, if necessary, be purified by a means such as washing or recrystallization by the use of the above-exemplified solvent for reaction.

1-6. General Formula (VII-1) or General Formula (VII-2)→a General Formula (II-1')

As the inert solvent usable in this reaction, any inert solvent may be used so long as it does not markedly inhibit the progress of the reaction. There can be used, for example, halogenated hydrocarbon solvents such as methylene chloride, chloroform, dichloroethane, chlorobenzene, etc.; nitrile solvents such as acetonitrile, propionitrile, etc.; aromatic hydrocarbon solvents such as toluene, xylene, etc.; organic acid solvents such as acetic acid, etc.; alcohol solvents such as methanol, ethanol, butanol, etc.; ester solvents such as ethyl acetate, butyl acetate, etc.; amide solvents such as N,N-dimethylformamide, N,N-dimethylacetamide, N-methylpyrrolidone, etc.; and water. These solvents may be used singly or as a mixture of two or more thereof.

As the catalyst usable in the reaction, there can be used tungstic acid, molybdic acid, vanadic acid, their salts, organic acids and inorganic acids. The organic acids include, for example, carboxylic acids such as formic acid, acetic acid, propionic acid, butyric acid, oxalic acid, adipic acid, dodecanedicarboxylic acid, lauric acid, stearic acid, trifluoroacetic acid, fumaric acid, maleic acid, benzoic acid, phthalic acid, etc.; and sulfonic acids such as methanesulfonic acid, 1,3-propanedisulfonic acid, p-toluenesulfonic acid, dodecylbenzenesulfonic acid, etc. The inorganic acids include hydrochloric acid, sulfuric acid, nitric acid, carbonic acid, boric acid and the like. In general, the amount of the catalyst used is usually about 1/10000 equivalent to about 3 equivalents, preferably about 1/1000 equivalent to about 1 equivalent, per equivalent of the compound of formula (VII-1) or formula (VII-2). The above-exemplified catalysts may be used singly or as a mixture of two or more thereof.

The oxidizing agent includes, for example, peracids (e.g. m-chloroperbenzoic acid, peracetic acid and performic acid), potassium metaperiodate, sodium hypochlorite, potassium hydrogenpersulfate (Oxon), sodium persulfate, potassium persulfate, ammonium persulfate, hydrogen peroxide, sodium perborate, N-chlorosuccinimide and N-bromosuccinimide. As to the amount of the oxidizing agent used, the oxidizing agent may be used in an amount properly chosen in the range of 1 to 2 equivalents per equivalent of the compound of general formula (VII-1) or formula (VII-2).

As to the reaction temperature, the reaction may be carried out in the range of −50° C. to the boiling point of the solvent used. Although the reaction time is varied depending on the scale of reaction, the reaction temperature and the like, it ranges from several minutes to 48 hours.

Since the reaction is an equimolar reaction, it is sufficient that the compound of general formula (VII-1) or general formula (VII-2) and the amine of general formula (V) or general formula (VIII) are used in equimolar amounts, though either of the reactants may be used in excess.

After completion of the reaction, the reaction solution can be subjected as it is to reaction in the subsequent step without isolating the compound of general formula (II-1'), i.e., the desired compound. When the isolation and/or purification of the desired compound are necessary, the desired compound in the reaction mixture is crystallized, followed by filtration and/or water-washing. Thus, the compound of general formula (II-1'), the desired compound can be obtained. Although the compound obtained has a satisfactory quality as it is in some cases, it can, if necessary, be purified by a means such as washing or recrystallization by the use of the above-exemplified solvent for reaction.

Production Process 2:

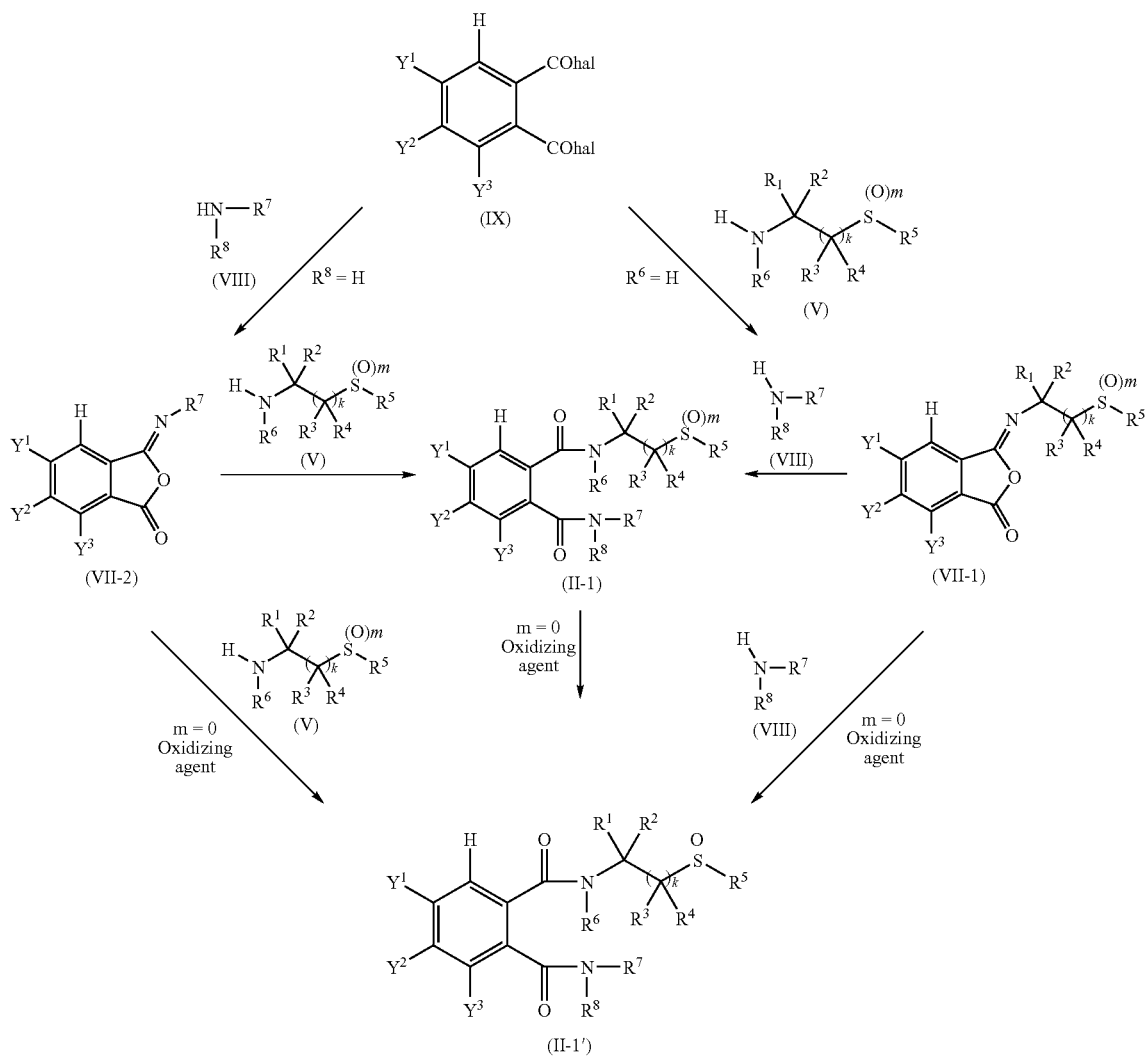

wherein $R^1$, $R^2$, $R^3$, $R^4$, $R^5$, $R^6$, $R^7 R^8$, $Y^1$, $Y^2$, $Y^3$, $Y^4$, k and m are as defined above, and hal is a halogen atom.

A phthaloyl dihalide of general formula (IX) used as a starting material in the reaction can be produced from a corresponding phthalic anhydride by a well-known process. The phthaloyl dihalide can be synthesized according to, for example, the process described in Organic Syntheses Coll. Vol. 2, 528, J. Org. Chem., 1973, 38, 2557, or the like.

The phthaloyl dihalide of general formula (IX) is allowed to react with an amine of general formula (V) in which $R^6$ is defined as a hydrogen atom in the presence or absence of an inert solvent and a base to obtain a compound of general formula (VII-1), and this compound (VII-1) is allowed to react with an amine derivative of general formula (VIII) in the presence of an inert solvent and in the presence or absence of a catalyst after or without isolation of the compound (VII-1), whereby a benzamide compound of general formula (II-1) can be produced.

In addition, the phthaloyl dihalide of general formula (IX) is allowed to react with an amine of general formula (VIII) in which $R^8$ is defined as a hydrogen atom in the presence or absence of an inert solvent and a base to obtain a compound of general formula (VII-2), and this compound (VII-2) is allowed to react with an amine derivative of general formula (V) in the presence of an inert solvent and in the presence or absence of a catalyst after or without isolation of the compound (VII-2), whereby a benzamide compound of general formula (II-1) can be produced.

Furthermore, a compound represented by general formula (II-1') corresponding to general formula (II-1) in which m is defined as 1 can be produced by oxidizing a compound of general formula (II-1) in which m is 0 with an oxidizing agent in an inert solvent in the presence or absence of a catalyst after or without isolation of the compound. The compound of general formula (II-1') can be produced also by allowing an amine of general formula (VIII) and an oxidizing agent to react at the same time or alternately with a compound of general formula (VII-1) in which m is defined as 0, in an inert solvent in the presence or absence of a catalyst after or without isolation of the compound of general formula (VII-1). In addition, the compound of general formula (II-1') can be produced also by allowing an amine of general formula (V) in which m is defined as 0 and an oxidizing agent to react at the same time or alternately with the compound of general formula (VII-2) in an inert solvent in the presence or absence of a catalyst after or without isolation of the compound of general formula (VII-2).

2-1. General Formula (IX)→General Formula (VII-1) or General Formula (VII-2)

In the case of this reaction, the desired compound can be produced according to, for example, the process disclosed in JP-A-2002-326989.

2-2. General Formula (VII-1) or General Formula (VII-2)→General Formula (II-1)

In the case of this reaction, the desired compound can be produced in the same manner as in production process 1-4.

2-3. General Formula (II-1)→General Formula (II-1')

In the case of this reaction, the desired compound can be produced in the same manner as in production process 1-5.

2-4. General Formula (VII-1) or General Formula (VII-2)→General Formula (II-1')

In the case of this reaction, the desired compound can be produced in the same manner as in production process 1-6.

EXAMPLES

The present invention is more concretely illustrated with the following examples and reference examples, which should not be construed as limiting the scope of the invention.

Example 1

Production of 2-iodo-6-methyl-N-[1,1-dimethyl-2-(methylsulfonyl)ethyl]benzamide

A mixture of 2-methyl-N-[1,1-dimethyl-2-(methylthio)ethyl]benzamide (2.37 g), tetrahydrofuran (20 mL), N-iodosuccinimide (2.30 g) and palladium acetate (0.22 g) was stirred with heating at 70° C. for 2 hours. The solvent was distilled off under reduced pressure and the resulting concentrate was dissolved in 1,2-dichloroethane (20 mL). The resulting solution was washed with an aqueous sodium thiosulfate solution and water, and the thus obtained organic layer containing 2-iodo-6-methyl-N-[1,1-dimethyl-2-(methylthio)ethyl]benzamide was used as it was in the subsequent step. To this solution were added acetic acid (0.60 g) and concentrated sulfuric acid (0.20 g), and to the resulting mixture was added 35% hydrogen peroxide (1.17 g). After stirring at 60° C. for 1 hour, 35% hydrogen peroxide (1.46 g) was added dropwise thereto at the same temperature and stirred for 3 hours. Then, an aqueous sodium sulfite solution was added dropwise to the reaction mixture at the same temperature to decompose the excess oxidizing agent. The reaction mixture was cooled and then neutralized with an aqueous sodium hydroxide solution. After the solvent was concentrated, the crystals precipitated were filtered, washed with water and then dried to obtain 3.24 g (yield 82%) of the title compound.

Physical property: melting point 134-136° C.

Example 2

Production of $N^2$-[1,1-dimethyl-2-(methyl-sulfonyl)ethyl]-3-iodo-$N^1$-(2-methyl-4-pentafluoroethyl-phenyl)-1,2-benzenedicarboxamide A mixture of $N^2$-[1,1-dimethyl-2-(methylthio)ethyl]-$N^1$-(2-methyl-4-pentafluoroethylphenyl)-1,2-benzenedicarboxamide (2.37 g), tetrahydrofuran (20 mL), N-iodosuccinimide (1.13 g) and palladium acetate (0.11 g) was stirred with heating at 70° C. for 2 hours. The solvent was distilled off under reduced pressure and the resulting concentrate was dissolved in 1,2-dichloroethane (20 mL). The resulting solution was washed with an aqueous sodium thiosulfate solution and water, and the thus obtained organic layer containing $N^2$-[1,1-dimethyl-2-(methylsulfinyl)ethyl]-3-iodo-$N^1$-(2-methyl-4-pentafluoroethylphenyl)-1,2-benzenedicarboxamide was used as it was in the subsequent step. To this solution were added acetic acid (0.30 g) and concentrated sulfuric acid (0.10 g), and to the resulting mixture was added 35% hydrogen peroxide (0.58 g). After stirring at 60° C. for 1 hour, 35% hydrogen peroxide (0.73 g) was added dropwise thereto at the same temperature and stirred for 3 hours. Then, an aqueous sodium sulfite solution was added dropwise to the reaction mixture at the same temperature to decompose the excess oxidizing agent. The reaction mixture was cooled and then neutralized with an aqueous sodium hydroxide solution. After the solvent was concentrated, the crystals precipitated were filtered, washed with water and then dried to obtain 2.56 g (yield 81%) of the title compound.

Physical property: melting point 143-144° C.

Example 3

Production of $N^2$-[1,1-dimethyl-2-(methyl-sulfonyl)ethyl]-3-iodo-$N^1$-(2,3,4-trichlorophenyl)-1,2-benzenedicarboxamide A mixture of $N^2$-[1,1-dimethyl-2-(methyl-sulfinyl)ethyl]-$N^1$-(2,3,4-trichlorophenyl)-1,2-benzenedicarboxamide (195.0 g), N,N-dimethylacetamide (780 mL), 1,3-diiodo-5,5-dimethylhydantoin (91.44 g) and palladium acetate (1.90 g) was stirred with heating at 80° C. for 3 hours. The solvent was distilled off under reduced pressure and the resulting concentrate was dissolved in 1,2-dichloroethane (780 mL). The resulting solution was washed with an aqueous sodium thiosulfate solution and water, and the thus obtained organic layer containing $N^2$-[1,1-dimethyl-2-(methyl-sulfinyl)ethyl]-3-iodo-$N^1$-(2,3,4-trichlorophenyl)-1,2-benzenedicarboxamide was used as it was in the subsequent step. To this solution were added formic acid (19.44 g) and concentrated sulfuric acid (16.57 g), and to the resulting mixture was added dropwise 35% hydrogen peroxide (49.25 g) at 60° C. After stirring at the same temperature for 1 hour, an aqueous sodium sulfite solution was added to the reaction mixture to decompose the excess oxidizing agent. The reaction mixture was cooled and then neutralized with an aqueous sodium hydroxide solution, and the crystals precipitated were filtered, washed with water and then dried to obtain 211.45 g (yield 83%) of the title compound.

Physical property: melting point 239-241° C.

Example 4

Production of $N^2$-[1,1-dimethyl-2-(methyl-sulfonyl)ethyl]-3-iodo-$N^1$-{2-methyl-4-[1,2,2,2-tetrafluoro-1-(trifluoromethyl)ethyl]phenyl}-1,2-benzenedicarboxamide A mixture of $N^2$-[1,1-dimethyl-2-(methyl-sulfinyl)ethyl]-$N^1$-{2-methyl-4-[1,2,2,2-tetrafluoro-1-(trifluoromethyl)ethyl]phenyl}-1,2-benzenedicarboxamide (2.80 g), N,N-dimethylacetamide (12 mL), 1,3-diiodo-5,5- dimethylhydantoin (1.1 g) and palladium acetate (2.5 mg) was stirred with heating at 80° C. for 2 hours. The solvent was distilled off under reduced pressure and the resulting concentrate was dissolved in 1,2-dichloroethane (12 mL). The resulting solution was washed with an aqueous sodium thiosulfate solution and water, and the thus obtained organic layer containing $N^2$-[1,1-dimethyl-2-(methylsulfinyl)ethyl]-3-iodo-$N^1$-{2-methyl-4-[1,2,2,2-tetrafluoro-1-(trifluoromethyl)-ethyl]phenyl}-1,2-benzenedicarboxamide was used as it was in the subsequent step. To this solution were added formic acid (0.24 g) and concentrated sulfuric acid (0.10 g), and to the resulting mixture was added dropwise 35% hydrogen peroxide (0.60 g) at 60° C. After stirring at the same temperature for 1 hour, an aqueous sodium sulfite solution was added to the reaction mixture to decompose the excess oxidizing agent. The reaction mixture was cooled and then neutralized with an aqueous sodium hydroxide solution, and the crystals precipitated were filtered, washed with water and then dried to obtain 3.07 g (yield 87%) of the title compound.

Physical property: melting point 213-217° C.

Example 5

Production of $N^2$-[1,1-dimethyl-2-(methyl-sulfonyl)ethyl]-3-iodo-$N^1$-{2-methyl-4-[1,2,2,2-tetrafluoro-1-(trifluoromethyl)ethyl]phenyl}-1,2-benzenedicarboxamide A mixture of $N^2$-[1,1-dimethyl-2-(methyl-sulfinyl)ethyl]-$N^1$-{2-methyl-4-[1,2,2,2-tetrafluoro-1-(trifluoromethyl)ethyl]phenyl}-1,2-benzenedicarboxamide (7.00 g), N,N-dimethylacetamide (28 mL), 1,3-diiodo-5,5-dimethylhydantoin (2.81 g) and palladium acetate (8.7 mg) was stirred with heating at 80° C. for 3 hours. The solvent was distilled off under reduced pressure and the resulting concentrate was dissolved in chlorobenzene (21 mL). The resulting solution was washed with an aqueous sodium thiosulfate solution and water, and the thus obtained organic layer containing $N^2$-[1,1-dimethyl-2-(methylsulfinyl)ethyl]-3-iodo-$N^1$-{2-methyl-4-[1,2,2,2-tetrafluoro-1-(trifluoromethyl)-ethyl]phenyl}-1,2-benzenedicarboxamide was used as it was in the subsequent step. To this solution were added formic acid (0.60 g) and concentrated sulfuric acid (0.52 g), and to the resulting mixture was added dropwise 35% hydrogen peroxide (1.51 g) at 80° C. After stirring at the same temperature for 3 hours, an aqueous sodium sulfite solution was added to the reaction mixture to decompose the excess oxidizing agent. The reaction mixture was slowly cooled and then neutralized with an aqueous sodium hydroxide solution, and the crystals precipitated were filtered, washed with water and then dried to obtain 7.73 g (yield 87%) of the title compound.

Example 6

Production of $N^2$-[1,1-dimethyl-2-(methyl-sulfonyl)ethyl]-3-iodo-$N^1$-{2-methyl-4-[1,2,2,2-tetrafluoro-1-(trifluoromethyl)ethyl]phenyl}-1,2-benzenedicarboxamide A mixture of $N^2$-[1,1-dimethyl-2-(methyl-sulfinyl)ethyl]-$N^1$-{2-methyl-4-[1,2,2,2-tetrafluoro-1-(trifluoromethyl)ethyl]phenyl}-1,2-benzenedicarboxamide (3.5 g), N,N-dimethylacetamide (14 mL), 1,3-diiodo-5,5-dimethylhydantoin (1.4 g) and palladium acetate (4.4 mg) was stirred with heating at 80° C. for 4 hours. The solvent was distilled off under reduced pressure and the resulting concentrate was dissolved in chlorobenzene (11 mL). The resulting solution was washed with an aqueous sodium sulfite solution and water, and the thus obtained organic layer containing $N^2$-[1,1-dimethyl-2-(methylsulfinyl)ethyl]-3-iodo-$N^1$-{2-methyl-4-[1,2,2,2-tetrafluoro-1-(trifluoro-methyl)ethyl]phenyl}-1,2-benzenedicarboxamide was used as it was in the subsequent step. To this solution were added N,N-dimethylacetamide (2 mL), formic acid (0.3 g) and concentrated sulfuric acid (0.25 g), and to the resulting mixture was added dropwise 35% hydrogen peroxide (0.76 g) at 70° C. After stirring at the same temperature for 3 hours, an aqueous sodium sulfite solution was added to the reaction mixture to decompose the excess oxidizing agent. The reaction mixture was slowly cooled and then neutralized with an aqueous sodium hydroxide solution, and the crystals precipitated were filtered, washed with water and then dried to obtain 3.90 g (yield 88%) of the title compound.

Example 7

Production of $N^2$-[1,1-dimethyl-2-(methyl-sulfonyl)ethyl]-3-iodo-$N^1$-{2-methyl-4-[1,2,2,2-tetrafluoro-1-(trifluoromethyl)ethyl]phenyl}-1,2-benzenedicarboxamide A mixture of $N^2$-[1,1-dimethyl-2-(methyl-sulfinyl)ethyl]-$N^1$-{2-methyl-4-[1,2,2,2-tetrafluoro-1-(trifluoromethyl)ethyl]phenyl}-1,2-benzenedicarboxamide (4 g), tetrahydrofuran (50 mL), palladium acetate (5.1 mg) and 1,3-diiodo-5,5-dimethylhydantoin (1.54 g) was stirred with heating at 70° C. for 2.5 hours. After completion of the reaction, the solvent was distilled off under reduced pressure and the resulting concentrate was dissolved in 1,2-dichloroethane (16 mL). The resulting solution was washed with an aqueous sodium thiosulfate solution and then saturated aqueous sodium chloride solution, and the thus obtained organic layer containing $N^2$-[1,1-dimethyl-2-(methylsulfinyl)ethyl]-3-iodo-$N^1$-{2-methyl-4-[1,2,2,2-tetrafluoro-1-(trifluoromethyl)ethyl]phenyl}-1,2-benzenedicarboxamide was used as it was in the subsequent step. To this solution were added formic acid (0.34 g) and concentrated sulfuric acid (0.15 g), and to the resulting mixture was added dropwise 35% hydrogen peroxide (0.86 g) at 60° C. After stirring at the same temperature for 3 hours, an aqueous sodium sulfite solution was added to the reaction mixture to decompose the excess oxidizing agent. The reaction mixture was slowly cooled and then neutralized with an aqueous sodium hydroxide solution, and the crystals precipitated were filtered, washed with water and then dried to obtain 4.21 g (yield 83%) of the title compound.

Example 8

Production of $N^2$-[1,1-dimethyl-2-(methyl-sulfonyl)ethyl]-3-iodo-$N^1$-{2-methyl-4-[1,2,2,2-tetrafluoro-1-(trifluoromethyl)ethyl]phenyl}-1,2-benzenedicarboxamide A mixture of $N^2$-[1,1-dimethyl-2-(methyl-sulfinyl)ethyl]-$N^1$-{2-methyl-4-[1,2,2,2-tetrafluoro-1-(trifluoromethyl)ethyl]phenyl}-1,2-benzenedicarboxamide (10.00 g), N,N-dimethylacetamide (40 mL), 1,3-diiodo-5,5-dimethylhydantoin (3.90 g) and palladium acetate (12.0 mg) was stirred with heating at 80° C. for 3 hours. The solvent was distilled off under reduced pressure and the resulting concentrate was dissolved in toluene (23 mL). The resulting solution was washed with an aqueous sodium thiosulfate solution and water, and the thus obtained organic layer containing $N^2$-[1,1-dimethyl-2-(methylsulfinyl)ethyl]-3-iodo-$N^1$-{2-methyl-4-[1,2,2,2-tetrafluoro-1-(trifluoromethyl)ethyl]phenyl}-1,2- benzenedicarboxamide was used as it was in the subsequent step. To this solution were added formic acid (0.80 g) and concentrated sulfuric acid (0.41 g), and to the resulting mixture was added dropwise 35% hydrogen peroxide (2.03 g) at 60° C. After stirring at the same temperature for 4 hours, an aqueous sodium sulfite solution was added to the reaction mixture to decompose the excess oxidizing agent. The reaction mixture was slowly cooled and then neutralized with an aqueous sodium hydroxide solution, and the crystals precipitated were filtered, washed with water and then dried to obtain 10.85 g (87% of the theoretical amount) of the title compound.

The compound of the above general formula (II) as intermediate can be produced according to a well-known process. The production of a compound of general formula (II-1) or (II-1') in which $Y^4$ is —CON($R^7$)$R^8$, as the compound of general formula (II) is described below as reference examples.

Reference Example 1

Production of $N^2$-[1,1-dimethyl-2-(methyl-thio)ethyl]-$N^1$-{2-methyl-4-[1,2,2,2-tetrafluoro-1-(trifluoromethyl)ethyl]phenyl}-1,2-benzenedicarboxamide A mixture of 2-methyl-1-methylthio-2-propanamine (11.61 g) and triethylamine (1.97 g) was added dropwise to a mixture of phthalic anhydride (14.42 g) and 1,2-dichloroethane (58 mL) at 50° C. The resulting mixture was stirred at the same temperature for 30 minutes to prepare N-[1,1-dimethyl-2-(methylthio)ethyl]phthalamic acid. Aqueous sodium hydrogencarbonate solution (9.81 g/101 mL) was added dropwise to this mixture at 40° C. and then methyl chloroformate (11.04 g) was added dropwise thereto at the same temperature. After completion of the dropwise addition, the reaction mixture was stirred at 50° C. for 1 hour and the organic layer was separated to prepare a solution of N-[1,1-dimethyl-2-(methylthio)ethyl]isophthalimide in 1,2-dichloroethane. This solution was added dropwise to a mixture of 2-methyl-4-[1,2,2,2-tetrafluoro-1-(trifluoro-methyl)ethyl]aniline (25.45 g), concentrated hydrochloric acid (0.49 g) and 1,2-dichloroethane (14.4 mL) at 60° C., and then stirred at 65° C. for 30 minutes. The reaction mixture was cooled and then neutralized with an aqueous sodium hydrogencarbonate solution, after which the organic layer was separated. The organic layer obtained was concentrated under reduced pressure, and the crystals precipitated were filtered, washed with water and then dried to obtain 47.06 g (yield 92%) of the title compound.

Reference Example 2

Production of $N^2$-[1,1-dimethyl-2-(methyl-sulfinyl)ethyl]-$N^1$-{2-methyl-4-[1,2,2,2-tetrafluoro-1-(trifluoromethyl)ethyl]phenyl}-1,2-benzenedicarboxamide A mixture of 2-methyl-1-methylthio-2-propanamine (11.61 g) and triethylamine (1.97 g) was added dropwise to a mixture of phthalic anhydride (14.42 g) and 1,2-dichloroethane (58 mL) at 50° C. The resulting mixture was stirred at the same temperature for 30 minutes to prepare N-[1,1-dimethyl-2-(methylthio)ethyl]phthalamic acid. Aqueous sodium hydrogencarbonate solution (9.81 g/101 mL) was added dropwise to this mixture at 40° C. and then methyl chloroformate (11.04 g) was added dropwise thereto at the same temperature. After completion of the dropwise addition, the reaction mixture was stirred at 50° C. for 1 hour and the organic layer was separated to prepare a solution of N-[1,1-dimethyl-2-(methylthio)ethyl]isophthalimide in 1,2-dichloroethane. This solution was added dropwise to a mixture of 2-methyl-4-[1,2,2,2-tetrafluoro-1-(trifluoro-methyl)ethyl]aniline (25.45 g), concentrated hydrochloric acid (0.49 g) and 1,2-dichloroethane (14.4 mL) at 60° C., and then stirred at 65° C. for 30 minutes to prepare a solution of $N^2$-[1,1-dimethyl-2-(methylthio)ethyl]-$N^1$-{2-methyl-4-{1,2,2,2-tetrafluoro-1-(trifluoromethyl)ethyl}phenyl}-1,2-benzenedicarboxamide in 1,2-dichloroethane. Formic acid (0.94 g) was added to this solution, followed by adding dropwise thereto 35% hydrogen peroxide (10.41 g) at 60° C. After completion of the dropwise addition, the resulting mixture was stirred at 60° C. for 1 hour and an aqueous sodium sulfite solution was added dropwise to the thus obtained reaction mixture at the same temperature to decompose the excess oxidizing agent. Then, the resulting mixture was neutralized with an aqueous sodium hydrogencarbonate solution, after which the organic layer was separated. The organic layer obtained was slowly cooled to 20° C. The crystals precipitated were filtered, washed with water and then dried to obtain 43.89 g (yield 83%) of the title compound.

Reference Example 3

Production of $N^2$-[1,1-dimethyl-2-(methyl-sulfinyl)ethyl]-$N^1$-(2,3,4-trichlorophenyl)-1,2-benzenedicarboxamide Phthaloyl dichloride (100.0 g) was added dropwise to a mixture of aqueous sodium hydroxide solution (40.39 g/300 mL), 2-methyl-1-methylthio-2-propanamine (61.66 g) and chloroform (300 mL) at 25° C. or lower. After completion of the dropwise addition, the resulting mixture was stirred at 20° C. for 30 minutes and the organic layer was separated to prepare a solution of N-[1,1-dimethyl-2-(methylthio)ethyl]isophthalimide in 1,2-dichloroethane. The previously prepared isophthalimide solution was added dropwise to a mixture of 2,3,4-trichloroaniline (91.93 g), p-toluenesulfonic acid monohydrate (2.34 g) and chloroform (75 mL) at 60° C. and then stirred for 30 minutes. Subsequently, formic acid (2.27 g) was added thereto and then 35% hydrogen peroxide (52.66 g) was slowly dropped thereinto with heating under reflux. Thereafter, the resulting mixture was stirred at 60° C. for 3 hours. An aqueous sodium sulfite solution was added dropwise to the thus obtained reaction mixture at the same temperature to decompose the excess oxidizing agent. Then, the resulting mixture was neutralized with an aqueous sodium hydrogencarbonate solution, after which the organic layer was separated. The organic layer obtained was heated at 60° C. Heptane (800 mL) was added dropwise thereto and the resulting mixture was slowly cooled to 20° C. The crystals precipitated were filtered, washed with water and then dried to obtain 202.44 g (yield 89%) of the title compound.

Reference Example 4

Production of $N^2$-[1,1-dimethyl-2-(methyl-sulfinyl)ethyl]-$N^1$-{2-methyl-4-[1,2,2,2-tetrafluoro-1-(trifluoromethyl)ethyl]phenyl}-1,2-benzenedicarboxamide Phthaloyl dichloride (18.78 g) was added dropwise to a mixture of aqueous sodium hydroxide solution (7.59 g/55 mL), 2-methyl-1-methylthio-2-propanamine (11.03 g) and 1,2-dichloroethane (55 mL) at 40° C. or lower. After completion of the dropwise addition, the resulting mixture was stirred at 40° C. for 30 minutes and the organic layer was separated to prepare a solution of N-[1,1-dimethyl-2-(methylthio)ethyl]isophthalimide in 1,2-dichloroethane. The previously prepared isophthalimide solution and 35% hydrogen peroxide (9.89 g) were slowly dropped at the same time into a mixture of 2-methyl-4-[1,2,2,2-tetrafluoro-1-(trifluoromethyl)ethyl]aniline (24.18 g), p-toluenesulfonic acid monohydrate (0.44 g) and 1,2-dichloroethane (13.75 mL) at 60° C. and then stirred at 60° C. for 1 hour. An aqueous sodium sulfite solution was added dropwise to the thus obtained reaction mixture at the same temperature to decompose the excess oxidizing agent. Then, the resulting mixture was neutralized with an aqueous sodium hydrogencarbonate solution, after which the organic layer was separated. The organic layer obtained was slowly cooled to 20° C. The crystals precipitated were filtered, washed with water and then dried to obtain 41.70 g (yield 83%) of the title compound.

Reference Example 5

Production of $N^2$-[1,1-dimethyl-2-(methyl-sulfinyl)ethyl]-$N^1$-{2-methyl-4-[1,2,2,2-tetrafluoro-1-(trifluoromethyl)ethyl]phenyl}-1,2-benzenedicarboxamide Sodium hydroxide (17.78 g) and sodium hydrogencarbonate (35.57 g) were dissolved in water (253 mL), followed by adding thereto 2-methyl-1-methylthio-2-propanamine (53 g) and 1,2-dichloroethane (253 mL), and to the resulting mixture was added dropwise phthaloyl dichloride (85.95 g) at 40° C. or lower. After completion of the dropwise addition, the resulting mixture was stirred at 40° C. for 30 minutes and the organic layer was separated to prepare a solution of N-[1,1-dimethyl-2-(methylthio)ethyl]isophthalimide in 1,2-dichloroethane. The previously prepared isophthalimide solution and 35% hydrogen peroxide (45.27 g) were slowly dropped at the same time into a mixture of 2-methyl-4-[1,2,2,2-tetrafluoro-1-(trifluoromethyl)ethyl]-aniline (110.7 g), p-toluenesulfonic acid monohydrate (2.01 g) and 1,2-dichloroethane (40 mL) at 60° C. and then stirred at 60° C. for 3 hours. An aqueous sodium sulfite solution was added dropwise to the thus obtained reaction mixture at the same temperature to decompose the excess oxidizing agent. Then, the resulting mixture was neutralized with an aqueous sodium hydrogencarbonate solution, after which the organic layer was separated. The organic layer obtained was slowly cooled to 20° C. The crystals precipitated were filtered, washed with water and then dried to obtain 184.11 g (yield 80%) of the title compound.

Reference Example 6

Production of $N^2$-[1,1-dimethyl-2-(methyl-sulfinyl)ethyl]-$N^1$-{2-methyl-4-[1,2,2,2-tetrafluoro-1-(trifluoromethyl)ethyl]phenyl}-1,2-benzenedicarboxamide Sodium hydroxide (0.83 g) and sodium hydrogencarbonate (1.66 g) were dissolved in water (12 mL), followed by adding thereto 2-methyl-1-methylthio-2-propanamine (2.62 g) and chlorobenzene (12 mL), and to the resulting mixture was added dropwise phthaloyl dichloride (4 g) at 40° C. or lower. After completion of the dropwise addition, the resulting mixture was stirred at 40° C. for 30 minutes and sodium chloride (1.73 g) was added thereto. Thereafter, the organic layer was separated to prepare a solution of N-[1,1-dimethyl-2-(methylthio)ethyl]isophthalimide in chlorobenzene. The previously prepared isophthalimide solution and 15% hydrogen peroxide (4.9 g) were alternately and slowly dropped into a mixture of 2-methyl-4-[1,2,2,2-tetrafluoro-1-(trifluoromethyl)ethyl]aniline (5.15 g), p-toluenesulfonic acid monohydrate (0.09 g) and chlorobenzene (3 mL) at 50° C. and then stirred at 60° C. for 3 hours. An aqueous sodium sulfite solution was added dropwise to the thus obtained reaction mixture at the same temperature to decompose the excess oxidizing agent. After neutralization with an aqueous sodium hydrogencarbonate solution, the resulting mixture was slowly cooled to 20° C. The crystals precipitated were filtered, washed with water and then dried to obtain 9.06 g (yield 85%) of the title compound.

The invention claimed is:
1. A process for producing a 2-halogenobenzamide compound represented by general formula (I):

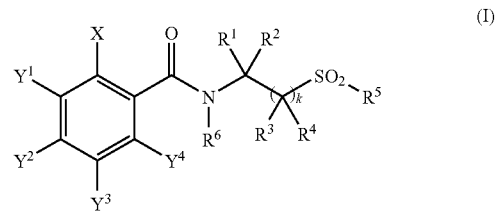

(wherein X, $R^1$, $R^2$, $R^3$, $R^4$, $R^5$, $R^6$, $Y^1$, $Y^2$, $Y^3$, $Y^4$ and k are as defined below), characterized by obtaining a benzamide compound represented by general formula (II):

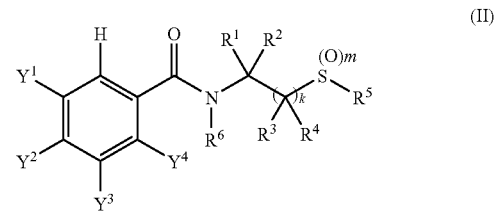

(wherein $R^1$, $R^2$, $R^3$, $R^4$, $R^5$, $R^6$, $Y^1$, $Y^2$, $Y^3$, $Y^4$, k and m are as defined below), by oxidation of a sulfide compound represented by the general formula:

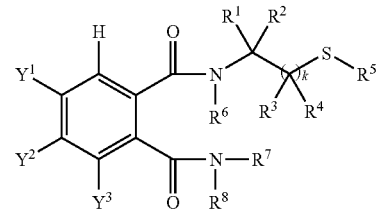

(wherein $R^1$, $R^2$, $R^3$, $R^4$, $R^5$, $R^6$, $R^7$, $R^8$, $Y^1$, $Y^2$, $Y^3$ and k are as defined below), allowing a halogenating agent to react with the benzamide compound represented by general formula (II),
(wherein each of $R^1$, $R^2$, $R^3$, $R^4$ and $R^6$, which may be the same or different, is a hydrogen atom or a ($C_1$-$C_6$)alkyl group, $R^5$ is a ($C_1$-$C_6$)alkyl group, k is 1 or 2, m is 1, $Y^4$ is —CON($R^7$)$R^8$ (wherein each of $R^7$ and $R^8$ are as defined below) and each of $Y^1$, $Y^2$ and $Y^3$ is a hydrogen atom $R^7$ and $R^8$, which may be the same or different, is a hydrogen atom; a ($C_1$-$C_6$) alkyl group; a phenyl group; or a substituted phenyl group having one or more substituents which may be the same or different and are selected from halogen atoms, cyano group, nitro group, $(C_1-C_6)$alkyl groups, $(C_1-C_6)$alkoxy groups, halo$(C_1-C_6)$alkyl groups and halo$(C_1-C_6)$alkoxy groups; in the presence of a palladium catalyst to obtain a substituted benzamide compound represented by general formula (III):

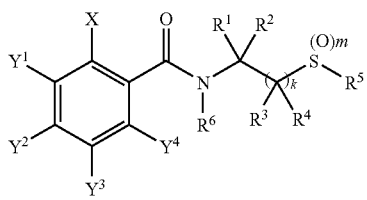

(III)

(wherein X is an iodine atom, and $R^1$, $R^2$, $R^3$, $R^4$, $R^5$, $R^6$, $Y^1$, $Y^2$, $Y^3$, $Y^4$, k and m are as defined above), and then allowing the substituted benzamide compound of general formula (III) obtained, to react with an oxidizing agent after or without isolating the substituted benzamide compound.

2. A process according to claim 1, wherein $R^7$ is H and $R^8$ is a substituted phenyl group having one or more substituents.

3. A process according to claim 2, wherein $R^8$ is a substituted phenyl group having two substituents.

4. A process according to claim 3, wherein $R^8$ is 2-methyl-4-{1,2,2,2-tetrafluoro-1-(trifluoromethyl)ethyl}phenyl.

* * * * *